United States Patent [19]

Bilweis

[11] Patent Number: 5,195,507
[45] Date of Patent: Mar. 23, 1993

[54] ENDOSCOPIC SURGICAL INSTRUMENT FOR DISPLACING TISSUE OR ORGANS

[75] Inventor: Joseph Bilweis, Noisy le Roi, France

[73] Assignee: Ethicon, Inc., Somerville, N.J.

[21] Appl. No.: 787,451

[22] Filed: Nov. 4, 1991

[30] Foreign Application Priority Data

Nov. 6, 1990 [FR] France .............................. 90 13711

[51] Int. Cl.⁵ .............................................. A61B 17/00
[52] U.S. Cl. ........................................ 128/20; 604/97;
604/99; 606/1; 606/191
[58] Field of Search ................ 128/3, 20; 604/96-99,
604/104, 105; 606/1, 191-199

[56] References Cited

U.S. PATENT DOCUMENTS

| | | | |
|---|---|---|---|
| 6,796 | 10/1849 | Haile | 606/199 |
| 157,343 | 12/1874 | Molesworth | 606/192 |
| 318,535 | 5/1885 | Bihler | 604/105 |
| 734,498 | 7/1903 | Bachler | 606/192 |
| 901,376 | 10/1908 | Roberts | 606/192 |
| 923,303 | 6/1909 | Shults | 606/193 |
| 1,213,005 | 1/1917 | Pillsbury | 606/192 |
| 2,032,859 | 3/1936 | Wappler | 604/97 |
| 3,841,304 | 10/1974 | Jones | 604/99 |
| 3,841,317 | 10/1974 | Awais | 128/17 |
| 3,863,639 | 2/1975 | Kleaveland | 606/148 |
| 4,744,363 | 7/1986 | Hasson . | |

FOREIGN PATENT DOCUMENTS 2071502 3/1990 United Kingdom .

*Primary Examiner*—Stephen C. Pellegrino
*Assistant Examiner*—Glenn Dawson
*Attorney, Agent, or Firm*—Emil Richard Skula

[57] ABSTRACT

A surgical instrument, in particular for endoscopic surgery, the instrument comprising a tube designed to be connected at its distal end to inflation/deflation means and provided at its proximal end with an inflatable spatula which communicates with the inflation/deflation means via a tube.

8 Claims, 2 Drawing Sheets

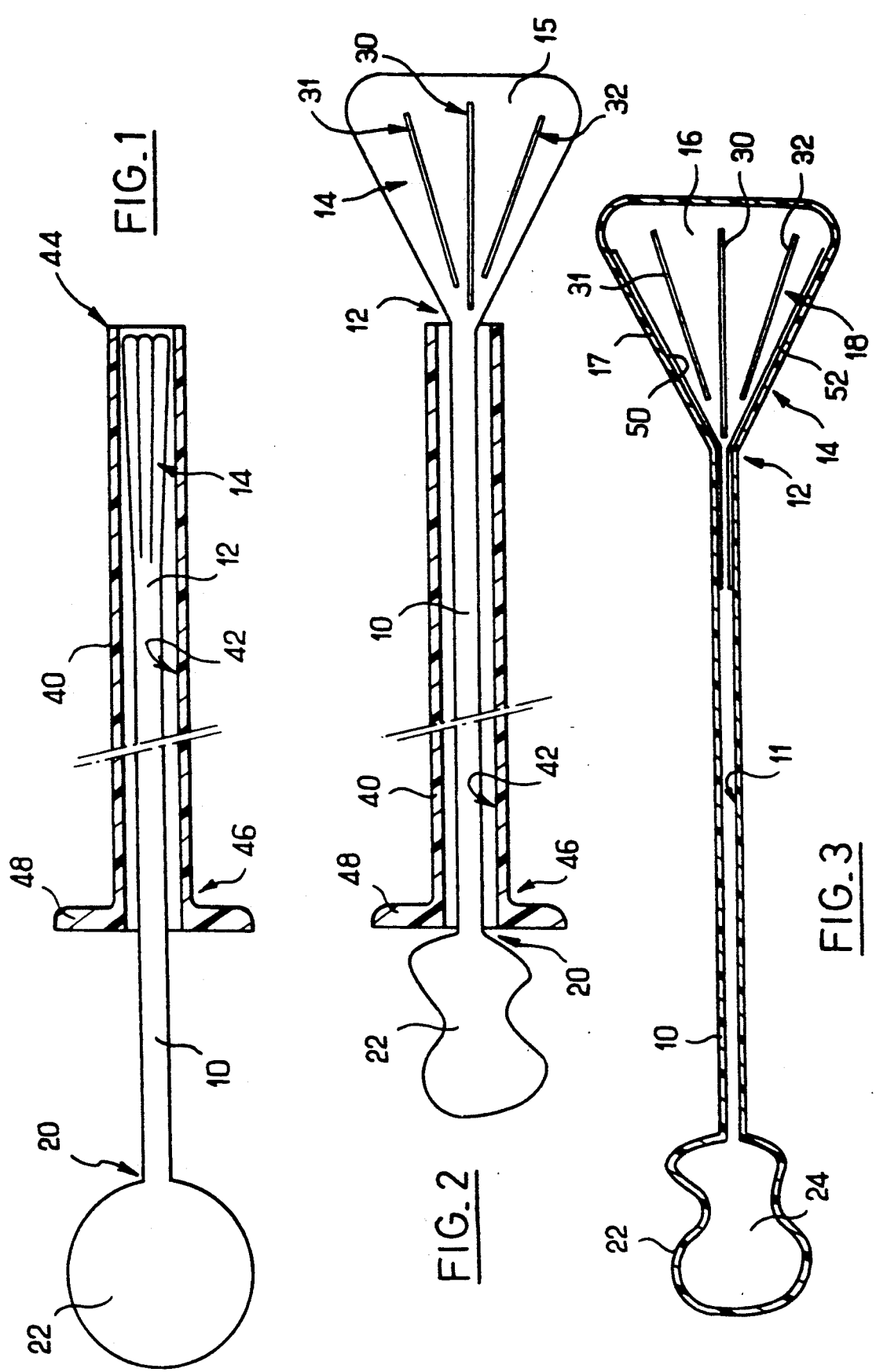

5,195,507

ENDOSCOPIC SURGICAL INSTRUMENT FOR DISPLACING TISSUE OR ORGANS

The present invention relates to the field of surgical instruments.

The present invention relates more particularly to the field of endoscopic surgery.

BACKGROUND OF THE INVENTION

Surgeons are aware that the instruments proposed so far for taking hold of and/or displacing tissues and/or organs, particularly during endoscopic surgery, do not give full satisfaction.

These instruments are generally in the form of forceps or the equivalent and they frequently traumatize the tissues or the organs they have taken hold of.

An object of the present invention is to eliminate the drawbacks of known prior instruments.

SUMMARY OF THE INVENTION

According to the present invention, this object is achieved by a surgical instrument, in particular for endoscopic surgery, comprising a tube designed to be connected at its distal end to inflation/deflation means and provided at its proximal end with an inflatable spatula which communicates with the inflation/deflation means via the tube.

As used herein, the convention concerning the terms "proximal" and "distal" relates to being near or far from the site at which surgery is being performed. The active part of the instrument is said to be at its "proximal" end, the part held by the surgeon is said to be at its "distal" end.

According to another advantageous feature of the present invention, the inflation/deflation means are constituted by a bulb connected in sealed manner to the distal end of the tube.

According to another advantageous feature of the present invention, the inflatable spatula is generally fan-shaped.

According to another advantageous feature of the present invention, the tube is placed in a cannula.

BRIEF DESCRIPTION OF THE DRAWINGS

An embodiment of the invention is described by way of example with reference to the accompanying drawings, in which:

FIG. 1 is a diagrammatic view of a device of the present invention in a rest position retracted into a cannula;

FIG. 2 is a view of the same device in a deployed or working position; and

FIGS. 2 and 3a are a diagrammatic longitudinal section view through the instrument comprising the tube, the spatula-shaped bag, and the inflation/deflation bulb.

DETAILED DESCRIPTION

Figure 3A:
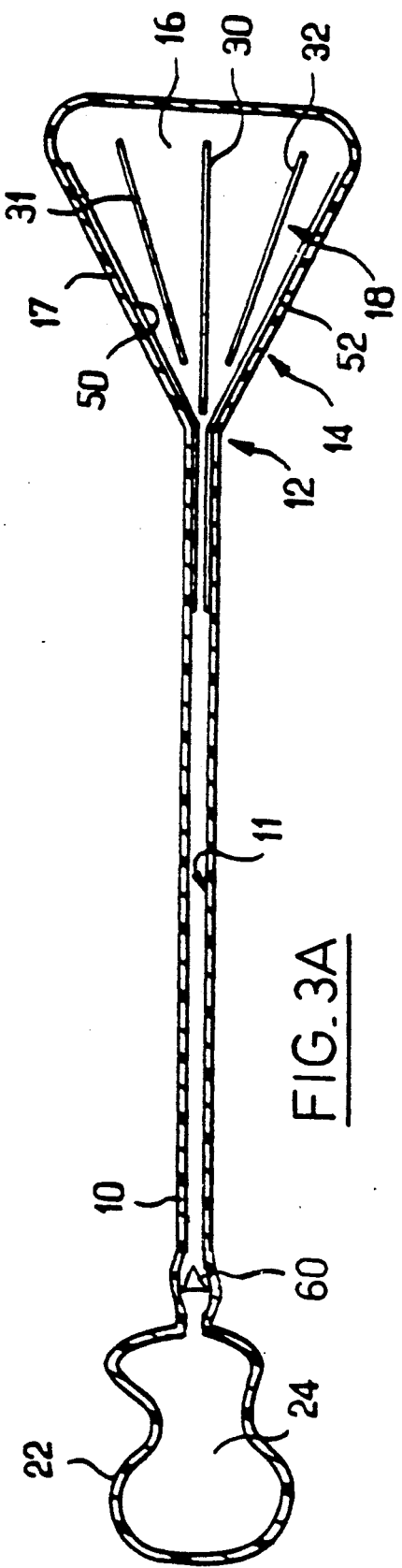

FIGS. 1 to 3 show an instrument suitable for displacing tissue or organs in a living being and essentially comprising a tube 10 provided at its proximal end 12 with an inflatable bag 14, and provided at its distal end 20 with a bulb 22.

The representation given in the accompanying figures is naturally diagrammatic and in particular the relative dimensions of the tube 10, of the inflatable bag 14, and of the bulb 22 as shown diagrammatically in the accompanying figures are not limiting in any way.

The inflatable bag 14 is generally fan-shaped when in the inflated state. That is to say the bag 14 is substantially plane. In plane view as shown in FIGS. 2 and 3, the inflatable bag 14 when in the inflated state is generally triangular in shape or in the shape of a sector of a cylinder.

The bag 14 is thus made from two main sheets 15 and 16 shown in FIGS. 2 and 3 which are generally parallel to each other in the inflated state and which are connected together at their peripheries by a transverse connecting wall 17. The main sheets 15 and 16 are parallel to the plane of FIGS. 2 and 3. The peripheral connection wall 17 extends generally transversely to the plane of FIGS. 2 and 3.

The spatula-forming inflatable bag 14 is preferably provided with longitudinal ribs or lines of stiffening. They are shown diagrammatically under references 30, 31, and 32 in FIGS. 2 and 3.

These figures thus show three stiffening ribs or lines. This number of stiffening ribs or lines is not limiting.

The stiffening ribs or lines 30, 31, or 32 converge towards the zone where the inflatable bag 14 joins the proximal end 12 of the tube 10.

The inside volume 18 of the inflatable bag 17 is in communication with the inside volume 24 of the inflating bulb 22 via the lumen 11 inside the tube 10. The tube 10, the inflatable bag 14, and the bulb 22 form an airtight closed system.

The tube 10, the inflatable bag 14, and the bulb 22 are preferably made in the form of a single piece. However, the tube 10, the inflatable bag 14, and the bulb 22 could be made in the form of pieces that are initially separate and are then assembled together by any technique known to the person skilled in the art.

the material from which the bulb 22 is made must be elastic and flexible to enable it to return to its rest position as shown in FIG. 1 when action is not applied thereto. The tube 10, the inflatable bag 14, and the bulb 22 are preferably made of rubber. In a variant, resilient return means may be provided inside the bulb 22.

The stiffening ribs or lines 30, 31, and 32 may be made of the same basic material as the inflatable bag 14, in the form of localized thickenings in the wall thereof. In a variant, the stiffening ribs or lines 30, 31, and 32 may be added to the bag 14.

Advantageously, and as shown diagrammatically in the accompanying figures, the tube 10 is placed in the lumen 42 of a cannula 40. The cannula 40 may be embodied in numerous different ways. The proximal end 44 of the cannula 42 is preferably rounded to avoid injuring the tissue or organs being displaced, and also to avoid injuring the tissues or organs surrounding those that are displaced by the spatula 14. The cannula 40 is also preferably provided at its distal end 46 with handle means such as a collar 48, for example.

When appropriate, the tube 10 may be received in a cannula 40 possessing a plurality of separate longitudinal lumens, with the other lumens being suitable for use in conventional manner e.g. to convey a flow of fluid for treatment or sampling purposes.

When the bulb 22 occupies its position of greatest extent, the inflatable spatula 14 is collapsed and folds longitudinally along its lines of stiffening 30, 31, and 32. The spatula 14 can thus be received in a retracted position inside the cannula 40. In this position, the spatula 14 can be brought to any appropriate selected point of a body by means of the cannula 40. Once the spatula 14 has been brought to its zone of use, it suffices merely to displace the tube 10 in translation relative to the cannula 40 and to compress the bulb 22, thereby inflating the spatula 14 in its position of use as shown in FIG. 2.

To withdraw the instrument, it then suffices to release the bulb 2. The spatula 14 then returns to its folded position and it can be retracted without difficulty into the cannula 40.

The instrument proposed by the present invention enables a large-sized spatula 14 to be deployed via a cannula 40 of small diameter. It may also be observed that because of the flexibility of the spatula 14 inherent to the material from which it is made, the instrument proposed in this manner by the present invention makes it possible in complete safety to avoid traumatizing in any way the tissues or organs that are displaced, and also to avoid traumatizing in any way the tissues or organs that come into contact with the cannula 40 while the instrument is being inserted or withdrawn.

Naturally the present invention is not limited to the particular embodiment described above, but extends to any variants coming within the spirit of the invention.

Where appropriate, a non-return valve 60 may be provided on the tube 10 to keep the spatula 14 deployed without requiring continuous action on the bulb 22. Naturally, the valve must be capable of being opened on request to retract the spatula 14.

The inflation/deflation bulb 22 may be replaced by any equivalent means, in particular by fluid feed means.

As shown diagrammatically in FIG. 3, the transverse connection wall 17 may be provided with two symmetrical blades 50 and 52 which extend along the proximal end of the tube 10. These blades 50 and 52 may be made of metal or of plastic. They serve to reinforce the instrument against forces acting transversely to the plane of FIGS. 2 and 3.

I claim:

1. A surgical instrument for endoscopic surgery, the instrument comprising a tube having a proximal end and distal end, inflation/deflation means comprising a bulb connected in a sealed manner to the distal end of the tube, and an inflatable fan-shaped spatula connected to said tube at its proximal end, said spatula being used for displaying tissues or organs and communicating with the inflation/deflation means via said tube, said tube placed in a cannula and extending at its distal end out of the cannula, said spatula made from two main sheets which are generally parallel to each other in the inflated state and which are connected together at their peripheries by a transverse connecting wall, said spatula being able to be received in a retracted position inside said cannula and said spatula provided with lines of stiffening.

2. An instrument according to claim 1, wherein the tube, the inflatable spatula, and the bulb are made in the form of a single piece.

3. An instrument according to claim 2, wherein the inflatable spatula is made of rubber.

4. An instrument according to claim 1, wherein the tube, the inflatable spatula, and the bulb are made separate and then assembled together.

5. An instrument according to claim 4, wherein the inflatable spatula is made of rubber.

6. An instrument according to claim 1, wherein the inflatable spatula is made of rubber.

7. An instrument according to claim 6, wherein the lines of stiffening are integrally molded with the spatula.

8. An instrument according to claim 1, wherein the lines of stiffening are made separate and then assembled to the inflatable spatula.

* * * * *